United States Patent [19]

McFarlane

[11] Patent Number: 4,500,312
[45] Date of Patent: Feb. 19, 1985

[54] CONNECTING ASSEMBLY

[76] Inventor: Richard H. McFarlane, 2571 Kaneville Rd., Geneva, Ill. 60134

[21] Appl. No.: 450,025

[22] Filed: Dec. 15, 1982

[51] Int. Cl.³ ............................................... A61M 5/00
[52] U.S. Cl. ...................................... 604/263; 604/192
[58] Field of Search ............... 604/165, 240, 242, 263, 604/192, 193

[56] References Cited

U.S. PATENT DOCUMENTS

| | | | |
|---|---|---|---|
| 1,591,761 | 7/1926 | Haines | 604/242 |
| 2,707,466 | 5/1955 | Hoskins et al. | 604/193 |
| 4,123,091 | 10/1978 | Cosentino et al. | 604/240 X |
| 4,192,305 | 3/1980 | Seberg | 604/165 |
| 4,362,156 | 12/1982 | Feller et al. | 604/165 |
| 4,430,080 | 2/1984 | Pasquini et al. | 604/263 X |

Primary Examiner—Dalton L. Truluck
Attorney, Agent, or Firm—John Cyril Malloy

[57] ABSTRACT

A connecting assembly used to form a removable but secure locking attachment between a protective sheath and a catheter structure such that a needle portion of the catheter is protected by being enclosed within the sheath and the sheath is prevented from inadvertent removal from the catheter structure.

5 Claims, 4 Drawing Figures

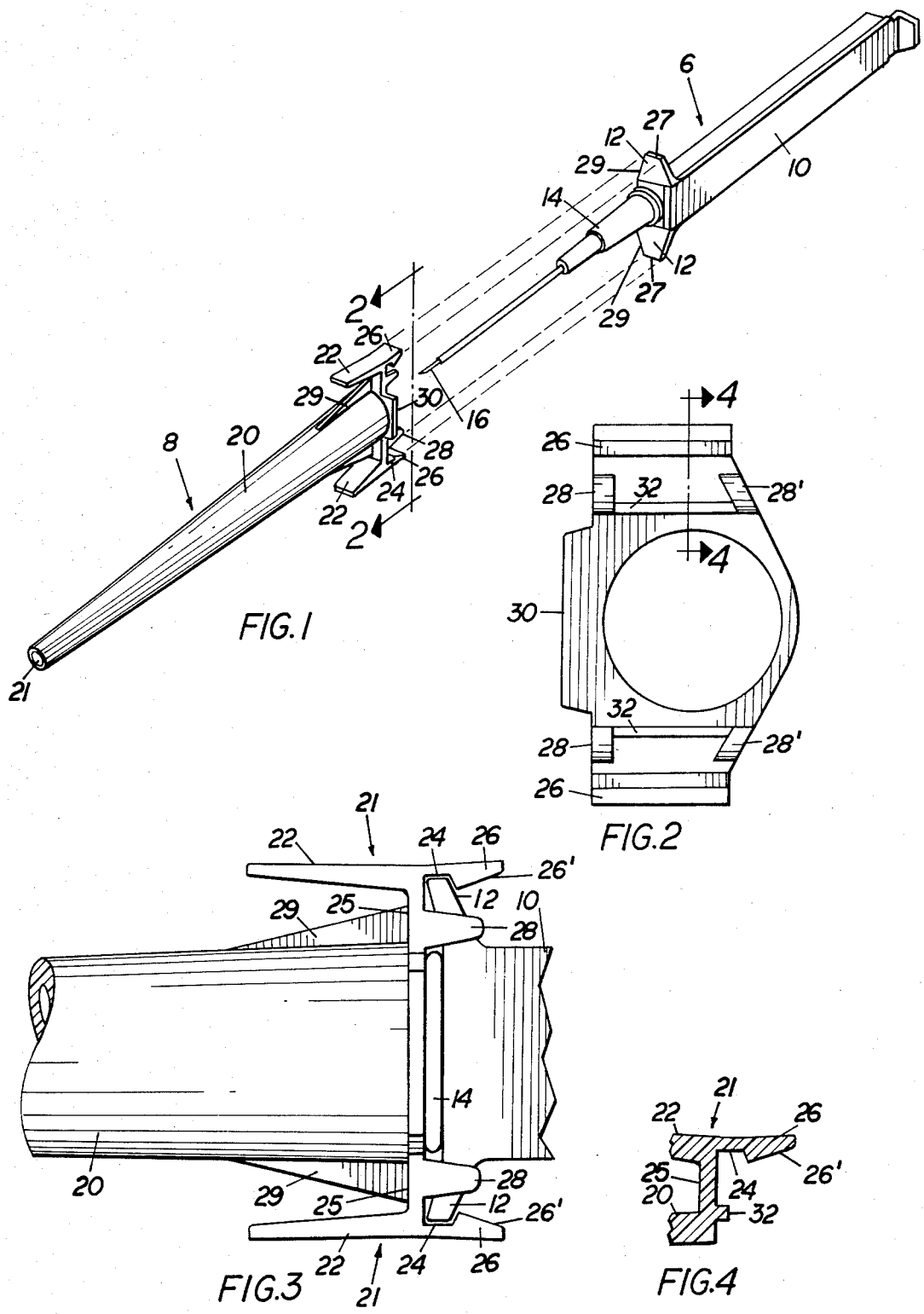

CONNECTING ASSEMBLY

BACKGROUND OF THE INVENTION

1. Field of the Invention

This invention relates to a connecting assembly including locking facilities for engaging the base portion of a catheter structure such that the needle portion or trocar and the attached cannula of such catheter structure is protected within a sheath type cover and the sheath is prevented from inadvertent removal from the catheter until the locking means is selectively activated causing release of the sheath from the catheter.

2. Description of the Prior Art

In the medical profession, catheters are commonly used with great frequency and because of such frequent and popular usage, numerous catheter designs including sheath or cover elements for the catheter structure have been designed. Common to all such protective covers is the requirement to adequately encase or house the cannula and trocar portions of the catheter. This is done not only for security reasons but to maintain proper sterility of the structure by keeping it out of contact with contaminating objects.

However, when it becomes necessary to use the catheter device on a patient, it is highly desirable in actual application for a sheath or cover structure to be readily removed from its protective position relative to the cannula. Such easy removal should be accomplished without unnecessary manipulation by the medical personnel involved.

While the prior art devices now in existence often accomplish the proper encasement or covering of the cannula, such sheaths or covering portions are frequently difficult to remove during the act of applying the catheter to the patient as intended. Further, structures specifically designed to accomplish ready removal of the sheath or protective structure often become disengaged inadvertently without the knowledge or intent of the medical personnel in charge. This results of course in a safety hazard or a ruining of the catheter inadvertently.

There is a need in the medical profession for a catheter structure having a cover or sheath portion adequately designed to securely engage the catheter in its covered or protected position. Such a connecting assembly should be capable of securely locking the catheter in place while at the same time having structural facilities for easy removal of the sheath from the remainder of the catheter through disengagement of a locking portion thereof in a selected fashion. Finally, the overall structural configuration and material as well as the design and dimensions of the intended catheter and protective sheath should be such as to allow the entire assembly to be disposable thereby allowing its production at a relatively low price.

SUMMARY OF THE INVENTION

The present invention is directed towards a connecting assembly of the type primarily designed for connecting in a locked or fixed position, a sheath or cover element over the cannula of a catheter device. Such a sheath or cover structure is of course utilized to protect the cannula for the purposes of safety as well as prevention of damage to the cannula or pointed tip of the catheter. The subject connecting assembly should also be structured to allow for the easy removal of the sheath as when applying the catheter to a patient.

More particularly, the catheter handle or base comprises flange means including oppositely disposed flange elements specifically configured and dimensioned to be lockingly embraced by a locking assembly. The locking assembly includes two oppositely disposed and substantially parallel locking fingers movably connected to the sheath element. The movable connection establishes a substantially pivotal interconnection between the respective locking fingers and the main portion of the sheath. This pivotal connection allows the locking fingers to move into and out of grasping or locking engagement with the distal ends or edges of each of the flange elements.

The locking fingers are specifically configured to include groove means. The groove means are in the form of individual grooves formed in the undersurface of the locking fingers and are configured and dimensioned to receive the distal edges of the flange elements therein. This interengagement between the flange elements and respective ones of the locking fingers is accomplished when the cannula is disposed in protective relation on the interior of the sheath or cover element.

Additional structural features of the locking assembly include guide means in the form of two pairs of guide projections. Each pair of projections is disposed to border and engage or be positioned immediately adjacent to oppositely disposed peripheral edges of the flange elements. In this manner, the flange elements are guided into proper locking position relative to the locking fingers. The distal end of the locking finger is then manipulated by the fingers of the personnel handling the catheter. Depression of such fingers towards one another allows for opening or spreading of the fingers so that the undersurface or groove portions integrally formed therein may grasp the distal edges of the respectively positioned flanges. It should be further noted that one guide projection of each pair is angularly disposed or oriented relative to the other of such pair so as to conform with a similar angular orientation of one of the peripheral edges of the flange element. This insures that the catheter is properly positioned within the sheath. In order to accomplish locking establishment between a given finger and a given flange, the angularly oriented guide projection and the angularly oriented peripheral edge of the flange element should be brought into mating engagement with one another.

Finally, the overall structural configuration of the connecting assembly and its position on the protective cover as well as the positioning of the flange elements on the catheter base is such as to allow removal of the cover or base from its protective position relative to the cannula by manipulating the two locking fingers with one hand when necessary.

BRIEF DESCRIPTION OF THE DRAWINGS

For a fuller understanding of the nature of the subject invention, reference should be had to the following detailed description taken in connection with the accompanying drawings, in which:

FIG. 1 is an isometric view wherein the various portions of the catheter and protective sheath or covering are separated.

FIG. 2 is an end view taken along line 2—2 of FIG. 1.

FIG. 3 is a detailed view in partial cutaway showing structural details of the connecting assembly when in its closed or locked position.

FIG. 4 is a sectional view in partial cutaway taken along line 4—4 of FIG. 2.

Similar reference characters refer to similar parts throughout the several views of the drawings.

DETAILED DESCRIPTION OF THE PREFERRED EMBODIMENT

The present invention is directed to a connecting assembly which is primarily designed, with reference to FIG. 1, to interconnect a catheter structure generally indicated as 6 in protective disposition within a cover or sheath element 8. More specifically, the catheter structure 6 includes a base or handle 10, pointed trocar 16, and cannula 14. The sheath cover is specifically configured to house the sharpened tip of the trocar 16 therein so as to prevent any unintended engagement of the catheter with any object.

The sheath element itself includes a base 20 which may have a truncated or tapering design and a distal end defined by aperture 21.

The connecting assembly includes flange means integrally or fixedly secured to the catheter 6 and comprising two flange elements 12 disposed in opposite, spaced apart relation and extending substantially outwardly from the catheter base 10 in transverse relation thereto but at a somewhat angular orientation. The connecting assembly of the present invention also includes a locking assembly including two spaced apart locking fingers generally indicated as 21 (FIG. 4). As best shown in FIGS. 1 and 3, the locking fingers are disposed in spaced apart relation to one another and extend substantially parallel both to one another and to the longitudinal axis of the sheath element 8. The locking fingers 21 are positioned in substantially spaced apart corresponding relation to the placement or disposition of the flange elements for adequate engagement thereof when the catheter 6 including trocar and cannula portions 16 and 14 respectively are brought into protective position within sheath element 8.

With reference to FIGS. 3 and 4, each locking finger comprises a distal end 22 and a front or leading end 26, wherein the finger itself is hingedly or pivotally connected to the sheath base 20 by a link means. As shown in FIGS. 3 and 4, this link means includes a link portion 25 integrally attached to each locking finger 21 and serving to interconnect the respective locking fingers 21 to the sheath base 20. Support braces 29 are also integrally secured to provide integrity and stability to the area surrounding the link portions 25. By virtue of the interconnection of the link means, the locking fingers are effectively pivotal about respective links portion 25 when the distal end 22 thereof is manipulated as by the fingers of the personnel using the catheter device. Depression of the distal ends 22 of each finger causes a counterclockwise rotation or spreading apart of ends 26 thereby effectively exposing the undersurface thereof. With reference to both FIGS. 1 and 3, the distal edges 27 of each flange element 12 is specifically constructed and configured to fit within a groove means in the form of two integrally formed groove elements 24. These groove portions 24 are formed on the undersurface of the locking fingers 21 such that when depression of the distal ends 22 occurs, these grooves are exposed to receive the distal edges 27 therein. Upon release of the distal ends 22 of each locking finger, the grooves effectively close over the distal edge 27 thereby maintaining an effective locking engagement between the groove 24 and the distal edge 27 of each of the flange elements 12. Further with regard to FIGS. 3 and 4, the undersurface portion 26' of each leading end 26 is angled inwardly so as to facilitate passage of the edges 27 of flanges 12 directly into the grooves 24 upon depression of the distal ends 22 of the fingers 21.

Further structural features of the subject invention includge guide means in the form of two pairs of guide projections. Each guide projection 28 and 28' of each pair is located to engage or be immediately adjacently positioned relative to a lateral peripheral boundary or edge 29 or 29' of the flange elements 12 when they are in their locking or closed position as shown in FIG. 3. Further, one guide projection 28' of each pair has a substantially angular orientation relative to the opposite guide projection 28 of each pair so as to conform to angular orientation of one of the peripheral edges 29 of flange 12. This insures proper orientation of the catheter 6 within the sheath element 8. This proper orientation is more clearly defined by the lateral projection or edge 30 being aligned with the face of the catheter base 10 as best shown in FIG. 1.

In addition, an interconnecting rib 32 is positioned between the various projections 28 and 28' of each pair and serves at a bracing function to the overall connector assembly.

It is therefore readily apparent that the flange elements 12, and more particularly the distal edges thereof 27, are engageable within grooves 24 on the undersurface of each locking finger 21. Depression of distal ends 22 of each locking finger causes the exposure of the grooves to such distal edges 27 and release of such distal ends causes the distal edges 27 to be received within grooves 24 and be embraced thereby in a locking position. Release of the catheter 6 from the protective sheath or covering 8 is accomplished in the same manner. Depression of the distal ends 22 towards the base 20 causes the release of the distal edges 27 of flange elements 12 and the ready removal of the catheter from the protective covering or sheath 8.

The invention accordingly comprises the features of construction, combination of elements and arrangement of parts which will be exemplified within the scope of the invention as indicated in the claims.

What is claimed is:

1. A connecting assembly used in combination with a catheter means and mounted at least in part on said catheter means and on a sheath element positionable in covering relation to a portion of said catheter means, said connecting assembly comprising:
    (a) flange means including two flange elements mounted on said catheter means and each extending outwardly therefrom in an opposite direction to one another and substantially transversely to a longitudinal axis of said catheter means,
    (b) a locking assembly including two locking fingers mounted on said sheath element in spaced apart relation and each disposed for engagement with one of said flange elements,
    (c) two link elements integrally formed on said sheath element and each attached in interconnecting relation between said sheath element and one of said locking fingers, each of said locking fingers pivotal about said link element into and out of attached relation with the respectively positioned flange element, each of said locking fingers disposed and structured for substantially overlapping engagement with a respective flange element including groove means integrally formed in an undersurface of each locking finger, (e) each of said groove means correspondingly dimensioned and configured relative to a distal edge of said respectively positioned flange element and disposed for selective, substantially surrounding reception of said distal edge therein, upon selective pivotal movement of said flange element, (f) guide means mounted on and extending outwardly from said sheath element in substantially parallel relation to a leading end of each locking finger, said guide means comprising two pairs of projections, each pair adjacent to one of said locking fingers and each projection thereof spaced apart a sufficient distance to border oppositely disposed lateral peripheral edges of each flange element adjacent said distal edge thereof, (g) each of said locking fingers and one respectively positioned pair of projection collectively disposed in surrounding engagement with a peripheral portion of one of said flange elements, whereby each flange element and said catheter means attached thereto being mounted in fixed, attached position relation to said sheath element upon connection of the flange means with said locking fingers and said guide means.

2. A connecting assembly as in claim 1 wherein at least one projection of each pair has an angular orientation in substantial conformance with an angularly configured peripheral edge of each flange element, said guide projections disposed in engageable relation to peripheral boundaries of said flange element.

3. A connecting assembly as in claim 1 wherein each of said locking fingers are selectively pivotal about said respective locking elements and positionable between an opened and a closed position relative to said respectively positioned flange elements upon respective depression and release of a distal end of each locking finger.

4. A connecting assembly as in claim 1 wherein each of said leading ends include a substantially angularly oriented undersurface extending in an inwardly diverging relation from an outer extremity thereof towards said respective groove means.

5. A connecting assembly as in claim 1 wherein each of said flange elements extend outwardly from said catheter means in an angularly oriented, substantially diverging relation to one another and to a central longitudinal axis of said catheter means.

* * * * *